United States Patent [19]
Descorps et al.

[11] Patent Number: 6,002,043
[45] Date of Patent: Dec. 14, 1999

[54] PHOSGENATION UNDER PRESSURE OF ACIDS AND OF ANHYDRIDES OF ACID CHLORIDES

[75] Inventors: Jean-Claude Descorps, Paris; Francois Metz, Irigny, both of France

[73] Assignee: Rhone-Poulenc Agrochimie Department Propriete Industrielle, Lyon Cedex, France

[21] Appl. No.: 08/971,406

[22] Filed: Nov. 17, 1997

Related U.S. Application Data

[63] Continuation-in-part of application No. 08/807,006, Feb. 26, 1997, abandoned.

[51] Int. Cl.[6] .................................................... C07C 51/58
[52] U.S. Cl. ............................................................ 562/857
[58] Field of Search ............................................... 562/857

[56] References Cited

FOREIGN PATENT DOCUMENTS

| | | |
|---|---|---|
| 0 220 516 A1 | 5/1987 | European Pat. Off. . |
| 0 531 826 A2 | 3/1993 | European Pat. Off. . |
| 2 232 532 | 1/1975 | France . |
| 402328 | 4/1932 | United Kingdom . |

*Primary Examiner*—Paul J. Killos
*Attorney, Agent, or Firm*—Morgan, Finnegan, LLP

[57] ABSTRACT

Process for the phosgenation of monocarboxylic acids and/or anhydrides, characterized in that the acid and/or the anhydride is treated, in the presence or absence of solvent, with a molar excess of phosgene, preferably 2 to 15 times as much phosgene as acid, at temperatures between 80 and 200° C. and at pressures between 2 and 60 bar, with or without catalyst, preferably in the absence of any catalyst.

Process furthermore characterized in that pressure is used to facilitate the separation of the hydrochloric acid, the carbon dioxide and the phosgene, in a column which is external to the reactor.

13 Claims, 1 Drawing Sheet

PHOSGENATION UNDER PRESSURE OF ACIDS AND OF ANHYDRIDES OF ACID CHLORIDES

U.S. patent application Ser. No. 08/807,006 was filed Feb. 26, 1997, now abandoned for which priority is hereby claimed under 35 U.S.C. §120.

The present invention relates to a novel process for gaining access to acid chlorides by phosgenation of monocarboxylic acids and/or corresponding anhydrides under pressure with or without catalyst, preferably in the absence of catalyst.

The conventional processes with catalyst consist in injecting phosgene into the acid by itself or in solution, at ordinary pressure and at temperatures between 80 and 150° C. An excess of phosgene is generally used. The vent gases, consisting of a mixture of phosgene, carbon dioxide and hydrochloric acid, are not separable at ordinary pressure unless very low temperature condensers are used, which always gives rise to a loss of phosgene.

The chemistry is governed by the following reaction equations:

(1) $RCOOH + COCl_2 \rightarrow RCOCl + HCl + CO_2$     (k1)

(2) $RCOOH + RCOCl \leftrightarrow (RCO)_2O + HCl$     (k-2/k2)

(3) $(RCO)_2O + 2COCl_2 \rightarrow 2RCOCl + 2CO_2$     (k3)

At ordinary pressure, reaction (1) is limited by the phosgene concentration, which is a function of the temperature. The disappearance of the acid is thus relatively rapid but the acid chloride formed reacts with the acid present to give the anhydride according to reaction (2), the subsequent conversion of which anhydride into acid chloride is slow (reaction (3)).

Thus, in order to activate reaction (3), it is necessary to use one or more catalysts, and there is consequently an abundance of literature for such catalysts. However, the use of a catalyst presents many drawbacks. Firstly, their cost and then their influence on the choice of materials, since the catalysts often make the reaction system very corrosive. Next, it promotes the formation of side products (eg. ketene) and the development of colour. Lastly, it involves purification of the acid chloride by distillation or crystallization.

As an example of such a process, mention will be made, for example, of French patent application FR 2,585,351 (EP 213,976), which describes the preparation of acid chlorides by phosgenation of the corresponding carboxylic acid. This document presents as a necessity the use of a catalyst in order to obtain acid chlorides under economically acceptable conditions. One of the subjects of EP 213,976 relates in particular to the catalyst used to carry out the phosgenation reaction.

Moreover, the Applicant in EP 213,976 cites as a document of the prior art an American patent (U.S. Pat. No. 2,657,233) which, according to the Applicant, discloses the use of a high pressure combined with a high temperature to produce acid chlorides. However, reading that document shows that the invention relates, in that case, to a process for the production of dicarboxylic acid chlorides by phosgenation, under high pressure and temperature, of the corresponding dicarboxylic acid. This document correctly teaches that for the production of acid monochlorides, the conventional method as described above is entirely satisfactory and that, ultimately, an improvement can only be expected by optimizing the catalysts used, which is confirmed by the abovementioned document FR 2,585,351 and documents FR 2,254,547 or EP 545,774, for example. The invention seeks to avoid the abovementioned drawbacks, in particular those associated with the use of catalysts in the prior art.

The invention provides a process for the phosgenation of monocarboxylic acids and/or anhydrides characterized in that the acid and/or the anhydride is treated, in the presence or absence of solvent, with a molar excess of phosgene, preferably 2 to 15 times (molar) as much phosgene as acid, at a temperatures from 80 to 200° C. and at a pressure from 2 to 60 bar (1 bar≈105 Pa), with or without catalyst, preferably in the absence of any catalyst. The process is generally performed in a closed system (autogenous pressure) or in an open system (pressure adjusted by eg partial degassing). The process is generally carried out as a continuous or semi-continuous process. Preferably, the process is performed in an open system by partially degassing. The degassing is generally carried out while taking care to ensure that an excess of phosgene remains. This occurs either by selective elimination of the hydrochloric acid and the carbon dioxide, while at the same time retaining the excess phosgene and a little HCl (so as not to make anhydride, but not too much, so as not to slow down the final reaction too much), or by a degassing including phosgene, the latter being resupplied at the same time. The temperature is advantageously chosen from 100 to 150° C., preferably from 110 to 130° C., whereas the pressure is preferably chosen from 6 to 40 bar. The temperature and pressure conditions are determined by the nature of the monocarboxylic acid and/or the anhydride and the corresponding chloride, in particular the critical point and/or the point of decomposition.

The advantages of the phosgenation under pressure according to the invention are to be able a) to dispense with the low temperature condensers and b) to dispense with solvent and/or catalyst. This makes it possible to avoid the final purification of the acid chloride obtained and allows a simple separation at the end of the reaction and a reduction in the utilities cost, and in general the advantages are those already discussed above associated with the absence of catalyst. It will be seen in Example 1 that the effect of adding a catalyst is virtually removed, that is to say that the gain in productivity obtained by the use of the process according to the invention with a catalyst compared with the same process without a catalyst is very low with regard to the drawbacks entailed by the use of such a catalyst. It will also be seen that the process according to the invention without a catalyst makes it possible to convert all of the acid employed into chloride in less time than a conventional process with catalyst would take. Lastly, the process according to the invention allows an increase in productivity when compared with the semi-continuous batch process at ordinary pressure.

The process according to the invention is advantageously used for the chlorination of acids of formula RCOOH into acid chloride RCOCl, R being defined as:

a linear or branched, saturated or unsaturated aliphatic radical having up to 22 carbon atoms, optionally substituted a) with one or more identical or different halogen atoms, b) with one or more nitro groups or c) with one or more aryl (preferably phenyl) aryloxy or arylthio groups, each of which is unsubstituted or substituted;

a cycloaliphatic radical having from 3 to 8 carbon atoms, which is unsubstituted or substituted by one or more substituents chosen a) from halogen atoms, b) alkyl or haloalkyl radicals, c) nitro groups and d) aryl, aryloxy and arylthio radicals, these aryl (preferably phenyl) or aryl derivatives being unsubstituted or substituted;

an aromatic carbocyclic radical which is unsubstituted or substituted by one or more substitutents chosen from the group consisting of halogen atoms, alkyl or haloalkyl radicals (preferably CF3) having from 1 to 12 carbon atoms, alkylthio or haloalkylthio radicals having from 1 to 6 carbon atoms, alkylsulphinyl or haloalkylsulphinyl radicals having from 1 to 6 carbon atoms, alkylsulphonyl or haloalkylsulphonyl radicals having from 1 to 6 carbon atoms, alkyloxy or haloalkyloxy radicals having from 1 to 6 carbon atoms, aryl, arylthio or aryloxy radicals and the nitro group;

an aromatic or non-aromatic 5- or 6-membered heterocyclic radical, having one or more identical or different heteroatoms chosen from oxygen, sulphur and nitrogen atoms and being unsubstituted or substituted by one or more substituents chosen from halogen atoms, nitro groups and alkyl, haloalkyl, alkyloxy, haloalkyloxy, aryl, arylthio and aryloxy radicals and/or optionally being fused to an aromatic carbocycle which is itself unsubstituted or substituted.

In general, when an aryl group (or one of the derivatives thereof such as aryloxy or arylthio) or an aromatic carbocycle is mentioned, it should be considered, even if this is not stated at the time when such a radical appears in order to abridge the present account, that this group may bear substituents chosen from the group consisting of halogen atoms and alkyl, haloalkyl, alkyloxy, haloalkyloxy, alkylthio, haloalkylthio, alkylsulphinyl, haloalkylsulphinyl, alkylsulphonyl, haloalkylsulphonyl, aryl, aryloxy, arylthio and nitro radicals.

The process according to the invention is also advantageously used for the chlorination of anhydrides of formula $(RCO)_2O$ or mixed anhydrides $(RCO)O(OCR')$ into acid chloride RCOCl and R'COCl, R and R' being defined as R above and R and R' not representing the same radical at the same time.

The process according to the invention is also suitable for the chlorination of mixtures of acids and anhydrides.

This process according to the invention is also characterized in that the pressure is moreover used to facilitate the separation of any hydrochloric acid, the carbon dioxide and the phosgene, in a column which is external to the reactor, without using low temperature condensers which, as we have already seen, are a cause of loss of $COCl_2$. The separation consequently becomes simpler, and therefore more economical, than with the known processes, and leads to phosgene which can be readily recycled and to pure hydrochloric acid.

The examples which follow illustre the invention. They show the advantages associated with the process according to the invention.

EXAMPLE 1

Production of Stearoyl Chloride by the Action of Phosgene on Stearic Acid (test No. 413).

0.175 g (0.615 mmol, concentration 0.41 M) of stearic acid and 0.920 g (8.171 mmol) of chlorobenzene are weighed out into a monocrystalline sapphire tube (1) with outside and inside diameters of 10 and 8 mm respectively, this tube being designed to withstand high pressures. A sealed tube (2) of diameter 5 mm containing deuterated benzene is also introduced into tube (1) to ensure the presence of an external lock, required for the subsequent NMR analysis. The tube (1) is then closed, immersed in an acetone/cardice bath (−78° C.) and then connected to a phosgene bottle. 0.606 g (6.127 mmol) of phosgene (concentration 4.08 M) is then condensed in tube (1). After warming to room temperature, the reaction medium is in the form of a suspension of stearic acid in a colourless, homogeneous liquid. The tube is then introduced into the cryomagnet of an NMR spectrometer preheated to 117° C. A first spectrum is recorded 11 min after introduction into the cryomagnet, i.e. a period corresponding to tuning of the spectrometer and to stabilization of the reactor at the set temperature. An automatic programme then allows the spectra to be recorded at regular intervals (typically every 5 min).

The molar percentage of each compound is determined by integration of the triplets corresponding to the methylenic protons alpha to the carbonyl function.

The following results are thus obtained.

| Test No. | Temp. ° C. | [Acid] M | [COCl2] M | Vol. ml | k observed* h − 1 | t ½ min. | p** g · h − 1 · 1 − 1 |
|---|---|---|---|---|---|---|---|
| 413 | 117 | 0.41 | 4.08 | 1.5 | 2.4 | 18 | 210 |

\* The kinetic constant k of pseudo-first order is calculated by linearization according to the formula: $-\text{Ln}(1-DC)=kt$ with DC=degree of conversion of the acid and t=time.

\*\* P=Productivity calculated at DC=50%.

By working as in the above example and varying different parameters (temperature, pressure, etc.), the results given in the tables below are obtained.

a) Influence of the temperature:

| Test No. | Temp. ° C. | [Acid] M | [COCl2] M | Vol. ml | k observed* h − 1 | t ½ min. | P g · h − 1 · 1 − 1 |
|---|---|---|---|---|---|---|---|
| 415 | 83 | 0.42 | 4.3 | 1.5 | 0.44 | 94 | 40 |
| 421 | 101 | 0.39 | 4.94 | 1.6 | 1.18 | 35 | 100 |
| 413 | 117 | 0.41 | 4.08 | 1.5 | 2.4 | 18 | 210 |
| 416 | 121 | 0.39 | 4.69 | 1.6 | 3.2 | 13 | 270 | b) Presence of the catalyst described in example 1 of FR 2,585,351:

| Test No. | Temp. °C. | [Acid] M | [COCl2] M | Vol. ml | k observed* h − 1 | t ½ min. | P g · h − 1 · 1 − 1 |
|---|---|---|---|---|---|---|---|
| 413* | 117 | 0.41 | 4.08 | 1.5 | 2.4 | 18 | 210 |
| 414** | 115 | 0.415 | 4.57 | 1.5 | 3.7 | 11 | 340 |

\* Without catalyst.
\*\* With catalyst (hexa n-butylguanidinium chloride)(0.02 mol %).

As has already been stated above, the effect of adding a catalyst is virtually erased, that is to say that the gain in productivity obtained by the use of the process according to the invention with catalyst compared with the same process without catalyst is very low.

c) Influence of the phosgene concentration:

| Test No. | Temp. °C. | [Acid] M | [COCl2] M | Vol. ml | k observed* h − 1 | t ½ min. | P g · h − 1 · 1 − 1 |
|---|---|---|---|---|---|---|---|
| 413 | 117 | 0.41 | 4.08 | 1.5 | 2.4 | 18 | 0210 |
| 420 | 114 | 0.47 | 3.15 | 1.3 | 2.1 | 20 | 185 | d) Influence of the solvent:

| Test No. | Temp. °C. | [Acid] M | [COCl2] M | Vol. ml | k observed* h − 1 | t ½ min. | P g · h − 1 · 1 − 1 |
|---|---|---|---|---|---|---|---|
| 415* | 93 | 0.42 | 4.3 | 1.5 | 0.44 | 94 | 40 |
| 425** | 80 | 0.865 | 10 | 1.4 | 0.63 | 66 | 50 |

\* Solvent=chlorobenzene.
\*\* Solvent COCl2.

e) Influence of degassing:

The influence of working with (test 417) or without (test 413) degassing is shown in the attached FIG. 1. Test 413 is already described and test 417 is the same but using 0.16 g (0.56 mmole) of acid, 0875 g of chlorobenzene and 0.88 g (8.9 mmol) of phosgene. For test 417, when 90% of acid is transformed (after about 45 min), the tube is allowed to cool in order to achieve degassing and then heated again up to 117° C. after 0.99 g of phosgene are again introduced.

DESCRIPTION OF THE DRAWING

Moreover, according to this FIG. 1, it is observed that a 100% degree of conversion of the stearic acid is obtained in less than 2 hours (about 75 min when the process is performed with degassing at 117° C. (test No. 417)). This makes it possible to compare our invention with the results given in FR 2,585,351. Indeed, in that document, the stearic acid is completely converted into chloride when the process is performed in the presence of 0.02 mol % of catalyst at a temperature of 120–125° C. but in 4 hours. It is therefore clearly seen, as has already been stated, that the process according to the invention without catalyst makes it possible to convert all of the acid employed into chloride in less time than a conventional process with catalyst would take.

EXAMPLE 2

Figure 1:
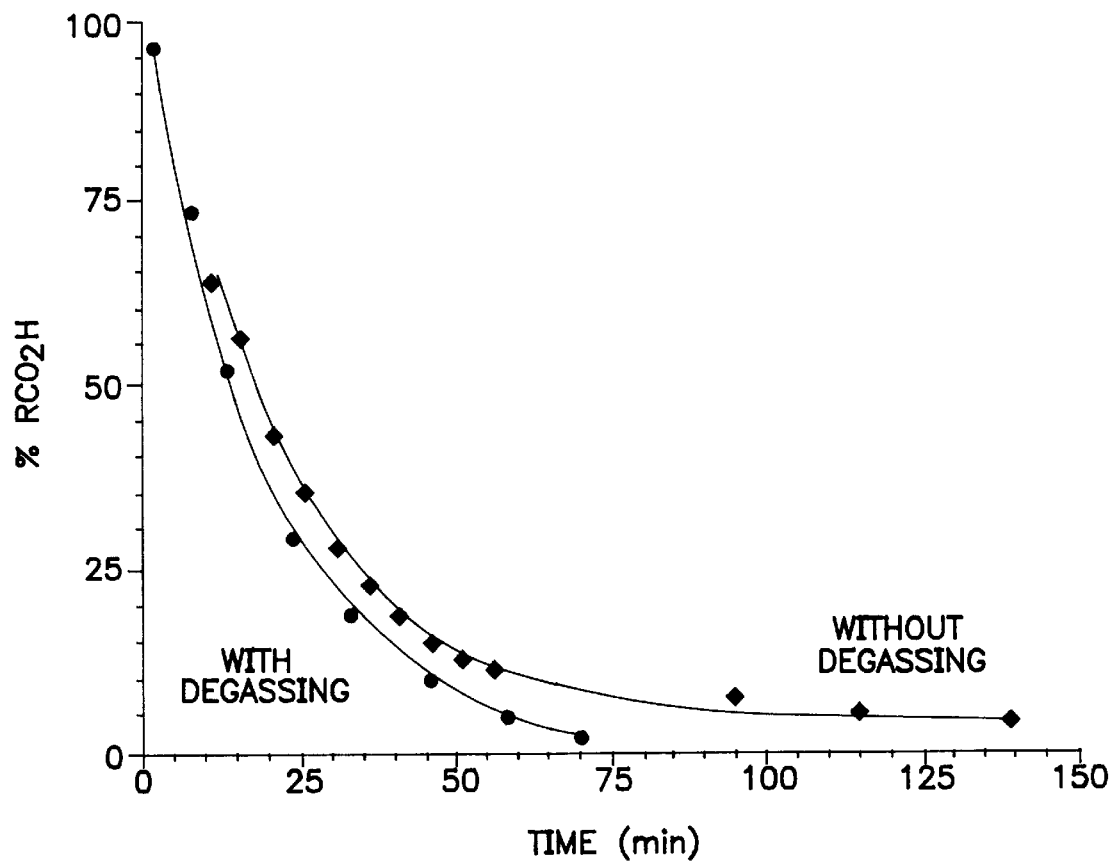

Phosgenation of Pivalic Acid:

a) A first approach was made by performing a phosgenation reaction under pressure on this neat acid. By working as in Example 1 with a 10 mm multinuclear probe but using deuterated pyridine for the lock in place of the deuterated benzene, it is seen that the phosgenation reactions under pressure of pivalic acid into acid chloride are first order. The results are as follows:

a1) at 81° C., a rate constant equal to 0.28 h-1 was found (conditions: 0.75 g of acid (7.3 mmol) and 1.5 g of phosgene (15.2 mmol)).

a2) at 115° C., a rate constant equal to 3.00 h-1 was found (conditions: 0.692 g of acid (6.78 mmol) and 1.25 g of phosgene (12.7 mmol)).

b) A second study is performed to monitor the kinetics of the phosgenation reaction of pivalic acid in chlorobenzene rather than with neat acid. In contrast with the study with neat acid, it is no longer possible to distinguish the CH3 protons of the acid and the chloride and, consequently, it is not possible to monitor the progress of the reaction in chlorobenzene.

We have, however, attempted to distinguish the acid and the chloride by carbon NMR since the chemical shifts (relative to tetramethylsilane, TMS) of the carbons of the carbonyl groups and the quaternary carbons of the tert-butyl groups are very different. Chemical shifts are obtained at 185.8 ppm for COOH, 180.8 for COCl, 38.9 ppm for the quaternary carbon of the acid and 49.5 ppm for the quaternary carbon of the acid chloride. An AMX 300 spectrometer operating at 75 MHz for the carbon 13 and equipped with a 10 mm multinuclear probe was used. The chemical shifts (δ) of the carbon resonance lines are expressed relative to tetramethylsilane (TMS). As in a), deuterated pyridine is used (external lock).

After that, monitoring was carried out which shows that, at 80° C., after 1 hour 45 minutes the acid chloride is predominant although a little acid remains (conditions: 0.06 g of acid (0.6 mmol), 0.943 g of chlorobenzene and 0.735 g of phosgene (7.43 mmol)).

EXAMPLE 3

Phosgenation of Pivalic Anhydride:

The proton NMR analyses under pressure were carried out on an AMX 300 spectrometer operating at 300 MHz for the proton and equipped with a 5 mm QNP 1H/13C/19F/31P gradient-z probe. The chemical shifts (δ) of the proton resonance lines are expressed relative to tetramethylsilane (TMS). Here and for example 4 to 6 as well, the monocrystalline sapphire tube has outside and inside diameters of 5 and 4 mm respectively.

As for the 1H NMR analysis under pressure of the phosgenation reaction of the neat acid (cf. 2a), it was possible to distinguish the CH3 protons of pivalic anhydride (δ=1.24 ppm) and of the acid chloride (δ=1.31 ppm).

The reaction was carried out at 80° C. with a 3 molar excess of phosgene relative to the anhydride.

When minus the natural logarithm of the relative molar proportion of pivalic anhydride is plotted as a function of time, a straight line is obtained. The apparent order of the reaction for the formation of pivaloyl chloride from pivalic anhydride is therefore 1. The slope of this straight line is equal to the rate constant for the reaction: k=1.6·10−2 min-1. The half-life t ½, representing the time required for the concentration of anhydide to decrease by one-half, is equal to ln 2/k (t ½=about 40 minutes).

EXAMPLE 4
Phosgenation of Octanoic Acid:

Working as in Example 2a), it is seen that the reactions for the phosgenation under pressure of neat octanoic acid into the acid chloride are first order. The results are as follows:

1) at 79° C., a rate constant equal to 0.25 h-1 was found (conditions: 0.79 g of acid (6.9 mmol) and 1.68 g of phosgene (17 mmol)).

2) at 124° C., a rate constant equal to 1.68 h-1 was found (conditions: 0.78 g of acid (6.85 mmol) and 1.35 g of phosgene (13.7 mmol)).

EXAMPLE 5
Phosgenation of Trifluoroacetic Acid:

Fluorine NMR analyses under pressure were carried out on an AMX 300 spectrometer operating at 300 MHz for the proton and equipped with a 5 mm QNP 1H/13C/19F/31P gradient-z probe. The chemical shifts of the fluorine resonance lines are expressed relative to trifluoroacetic acid (TFA).

The reaction is monitored by the appearance of a resonance line at 0.3 ppm, which corresponds to trifluoroacetyl chloride, the acid being at 0 ppm since it is the reference.

The reaction is slow since the degree of conversion into chloride is about 20% after heating at 107° C. for 4 hours. However, this phosgenation reaction under pressure with neat acid does take place (conditions: 0.22 g of acid (1.93 mmol) and 0.464 g of phosgene (4.7 mmol)).

EXAMPLE 6
Phosgenation of Benzoic Acid:

13C NMR analyses under pressure were carried out on an AMX 300 spectrometer operating at 75 MHz for carbon 13 and equipped with a 5 mm QNP 1H/13C/19F/31P gradient-z probe. The chemical shifts (δ) of the carbon resonance lines are expressed relative to tetramethylsilane (TMS).

It is very difficult by 1H NMR to distinguish benzoic acid from the acid chloride. For this reason, the test was carried out with benzoic acid enriched with carbon 13 (carbon of the carbonyl group) in order to carry out kinetic monitoring at 90° C. of the reaction under pressure of the neat acid by NMR on this carbon 13. Indeed, the carbon resonance lines of the acid and of the acid chloride are at δ=170 ppm and δ=167 ppm respectively.

When minus the natural logarithm of the relative molar proportion of benzoic acid is plotted as a function of time, a straight line is obtained (conditions: 0.077 g of acid (0.63 mmol) and 0.422 g of phosgene (4.27 mmol)-Temperature: 90° C.). The apparent order of the reaction for the formation of benzoyl chloride from benzoic acid is therefore 1. The slope of this straight line is equal to the rate constant for the reaction: k=0.28 h-1. The half life t ½, representing the time required for the concentration of acid to decrease by one-half, is equal to ln 2/k (t ½=about 2h 30).

General procedure for tests on a larger scale than the previous ones:

The following tests were performed in a two-liter autoclave reactor equipped with a condenser and a pressure-control system. The total volume of the autoclave and the accessories is 2.25 liters. Monochlorobenzene and the organic acid are introduced into the totally anhydrous reactor which has been flushed with argon, and phosgene is then added at about 20° C. The valve set to air is closed and the control valve is adjusted to the set opening for the desired pressure. The reaction medium is then brought to 120° C. as quickly as possible.

The percentages of acid, of anhydride and of chloride in the reaction medium are determined by proton NMR monitoring.

EXAMPLE 7
Phosgenation of Pivalic Acid:

61.3 g (0.6 mol) of pivalic acid and 890 g of monochlorobenzene are introduced into the reactor and 597 g (6 mol) of phosgene are then added over about 30 minutes while maintaining the temperature of the reaction medium at a maximum of 25° C. The set pressure is adjusted to 10.5 bar relative and the reaction medium is heated. About 0.3% anhydride forms in the first 30 minutes. The anhydride formed becomes phosgenated. The reaction is complete after two hours. The level of residual acid is less than 0.5 mol %, the level of residual anhydride is zero and the level of pivaloyl chloride obtained is greater than 99.5 mol %.

EXAMPLE 8
Phosgenation of 2-ethylhexanoic Acid:

87 g (0.6 mol) of 2-ethylhexanoic acid and 890 g of monochlorobenzene are introduced into the reactor and 607 g (6.14 mol) of phosgene are then added over about 30 minutes, while maintaining the temperature of the reaction medium at a maximum of 25° C. The set pressure is adjusted to 10.5 bar relative and the reaction medium is heated. The reaction is complete after one hour 30 minutes. The levels of residual acid and anhydride are zero and the level of 2-ethylhexanoyl chloride obtained is greater than 99.8 mol %.

EXAMPLE 9
Phosgenation of Octanoic Acid:

86.6 g (0.6 mol) of octanoic acid and 890 g of monochlorobenzene are introduced into the reactor and 600 g (6.07 mol) of phosgene are then added over about 30 minutes, while maintaining the temperature of the reaction medium at a maximum of 25° C. The set pressure is adjusted to 10.5 bar relative and the reaction medium is heated. After two hours, the level of residual acid is about 1 mol %, the level of residual anhydride is zero and the level of octanoyl chloride obtained is 99 mol %.

EXAMPLE 10
Phosgenation of Stearic Acid:

170.4 g (0.6 mol) of stearic acid and 890 g of monochlorobenzene are introduced into the reactor and 594 g (6 mol) of phosgene are then added over about 30 minutes, while maintaining the temperature of the reaction medium at a maximum of 25° C. The set pressure is adjusted to 10.5 bar relative. The reaction medium is heated to 120° C. and is maintained at this temperature for 1 hour 30 minutes and is then heated to 150° C. and maintained at this new temperature for 1 hour. The level of residual acid is then about 1.4 mol %, the level of residual anhydride is zero and the level of stearoyl chloride obtained 98.6 mol %. The maximum pressure reached was 9 bar relative.

EXAMPLE 11

Phosgenation of Oleic Acid:

200 g (0.7 mol) of oleic acid and 725 g of monochlorobenzene are introduced into the reactor and 574 g (5.8 mol) of phosgene are then added. The set pressure is adjusted to 11.2 bar relative and the reaction medium is heated. The reaction is complete after 1 hour 30 min. The level of residual acid is 0.5 mol % and the level of oleoyl chloride obtained is 99.5 mol %.

EXAMPLE 12

Phosgenation of p-toluic Acid:

81.4 g (0.6 mol) of p-toluic acid and 892 g of monochlorobenzene are introduced into the reactor and 582 g (5.9 mol) of phosgene are then added. The set pressure is adjusted to 11.2 bar relative and the reaction medium is heated. The reaction is complete after 3 hours. Analysis of the final reaction medium is carried out by gas chromatography. The level of residual acid is 0.3 mol % and the level of toluoyl chloride obtained is 99.7 mol %.

EXAMPLE 13

Phosgenation of 2-furoic Acid:

110 g (0.98 mol) of 2-furoic acid and 900 g of monochlorobenzene are introduced into the reactor and 615 g (6.2 mol) of phosgene are then added. The set pressure is adjusted to 11.2 bar relative and the reaction medium is heated. The pressure is adjusted by addition of argon. The reaction is complete after 3 hours. The level of residual acid is 5.5 mol % and the level of 2-furoyl chloride obtained is 94.5 mol %.

We claim:

1. Process for the phosgenation of monocarboxylic acids and/or anhydrides, characterized in that the acid and/or the anhydride is treated in the presence or absence of solvent, with molar excess of phosgene at temperatures from 80 to 200° C. and at a pressure from 2 to 60 bar, without catalyst, to obtain a monocarboxylic acid chloride.

2. Process according to claim 1 in which a 2 to 15 times molar excess of phosgene to acid is used.

3. Process according to claim 1, characterized in that the process is performed in an open system by partially degassing.

4. Process according to claim 1, characterized in that the temperature is from 100 to 150° C.

5. Process according to claim 4 in which the temperature is from 110 to 130° C.

6. Process according to claim 1, characterized in that the pressure is from 6 to 40 bar.

7. Process according to claim 1, characterized in that a monocarboxylic acid of formula RCOOH is converted into acid chloride RCOCl, R being defined as:

a linear or branched, saturated or unsaturated aliphatic radical having up to 22 carbon atoms, optionally substituted a) with one or more identical or different halogen atoms, b) with one or more nitro groups or c) with one or more aryl, aryloxy or arylthio groups, each of which is unsubstituted or substituted;

a cycloaliphatic radical having from 3 to 8 carbon atoms, which is unsubstituted or substituted by one or more substituents chosen a) from halogen atoms, b) alkyl or haloalkyl radicals, c) nitro groups and d) aryl, aryloxy and arylthio radicals, these aryl or aryl derivatives being unsubstituted or substituted;

an aromatic carbocyclic radical which is unsubstituted or substituted by one or more substituents chosen from the group consisting of halogen atoms, alkyl or haloalkyl radicals having from 1 to 12 carbon atoms, alkylthio or haloalkylthio radicals having from 1 to 6 carbon atoms, alkylsulphinyl or haloalkylsulphinyl radicals having from 1 to 6 carbon atoms, alkylsulphonyl or haloalkylsulphonyl radicals having from 1 to 6 carbon atoms, alkyloxy or haloalkyloxy radicals having from 1 to 6 carbon atoms, aryl, arylthio or aryloxy radicals and the nitro group;

an aromatic or non-aromatic 5- or 6-membered heterocyclic radical, having one or more identical or different heteroatoms chosen from oxygen, sulfur and nitrogen atoms and being unsubstituted or substituted by one or more substituents chosen from halogen atoms, nitro groups and alkyl, haloalkyl, alkyloxy, haloalkyloxy, aryl, arylthio and aryloxy radicals and/or optionally being fused to an aromatic carbocycle which is itself unsubstituted or substituted.

8. Process according to claim 1, characterized in that a mixture of acids and anhydride is converted to monocarboxylic acid chloride.

9. Process according to claim 7 characterized in that the separation of hydrochloric acid and carbon dioxide formed in the reactions and phosgene, is conducted in a column which is external to the reactor.

10. Process according to claim 1, wherein hydrochloric acid and carbon dioxide formed in the process are separated in an external separation zone.

11. Process according to claim 1, characterized in that an anhydride of formula $(RCO)_2O$ or mixed anhydride $(RCO)O(OCR')$ is converted into acid chloride RCOCl and R'COCl, wherein R or R' is defined as:

a linear or branched, saturated or unsaturated aliphatic radical having up to 22 carbon atoms, optionally substituted a) with one or more identical or different halogen atoms, b) with one or more nitro groups or c) with one or more aryl, aryloxy or arylthio groups, each of which is unsubstituted or substituted;

a cycloaliphatic radical having from 3 to 8 carbon atoms, which is unsubstituted or substituted by one or more substituents chosen a) from halogen atoms, b) alkyl or haloalkyl radicals, c) nitro groups and d) aryl, aryloxy and arylthio radicals, these aryl or aryl derivatives being unsubstituted or substituted;

an aromatic carbocyclic radical which is unsubstituted or substituted by one or more substituents chosen from the group consisting of halogen atoms, alkyl or haloalkyl radicals having from 1 to 12 carbon atoms, alkylthio or haloalkylthio radicals having from 1 to 6 carbon atoms, alkylsulphinyl or haloalkylsulphinyl radicals having from 1 to 6 carbon atoms, alkylsulphonyl or haloalkylsulphonyl radicals having from 1 to 6 carbon atoms, alkyloxy or haloalkyloxy radicals having from 1 to 6 carbon atoms, aryl, arylthio or aryloxy radicals and the nitro group;

an aromatic or non-aromatic 5- or 6-membered heterocyclic radical, having one or more identical or different heteroatoms chosen from oxygen, sulphur and nitrogen atoms and being unsubstituted or substituted by one or more substituents chosen from halogen atoms, nitro groups and alkyl, haloalkyl, alkyloxy, haloalkyloxy, aryl, arylthio and aryloxy radicals and/or optionally being fused to an aromatic carbocycle which is itself unsubstituted or substituted.

12. The process according to claim 7, wherein R is:

an aliphatic radical substituted with one or more phenyl groups;

a cycloaliphatic group substituted with a phenyl group; or an aromatic carbocyclic radical substituted with a $CF_3$ group.

13. The process according to claim 11, wherein R or R' is:

an aliphatic radical substituted with one or more phenyl groups;

a cycloaliphatic group substituted with a phenyl group; or an aromatic carbocyclic radical substituted with a $CF_3$ group.

* * * * *